US006787355B1

(12) United States Patent
Miller et al.

(10) Patent No.: US 6,787,355 B1
(45) Date of Patent: Sep. 7, 2004

(54) MULTIPOTENT NEURAL STEM CELLS FROM PERIPHERAL TISSUES AND USES THEREOF

(75) Inventors: Freda D. Miller, Montreal (CA); Andrew Gloster, Saskatoon (CA); Jean Toma, Montreal (CA)

(73) Assignee: McGill University, Montreal (CA)

( * ) Notice: Subject to any disclaimer, the term of this patent is extended or adjusted under 35 U.S.C. 154(b) by 83 days.

(21) Appl. No.: 09/670,049

(22) Filed: Sep. 25, 2000

Related U.S. Application Data

(63) Continuation-in-part of application No. 09/490,422, filed on Jan. 24, 2000, which is a continuation-in-part of application No. 08/920,272, filed on Aug. 22, 1997.
(60) Provisional application No. 60/024,456, filed on Aug. 27, 1996, and provisional application No. 60/024,590, filed on Aug. 26, 1996.

(51) Int. Cl.[7] ............................ C12N 5/00; C12N 5/02; C12N 15/00
(52) U.S. Cl. ....................... 435/377; 435/378; 435/375; 435/383; 435/325
(58) Field of Search ................................ 435/377, 387, 435/375, 383, 325, 7.21

(56) References Cited

U.S. PATENT DOCUMENTS

| | | | | |
|---|---|---|---|---|
| 5,318,907 A | * | 6/1994 | Ronnette et al. | 435/240.21 |
| 5,338,839 A | | 8/1994 | McKay et al. | |
| 5,753,506 A | | 5/1998 | Johe | |
| 5,824,489 A | * | 10/1998 | Anderson et al. | 435/7.21 |
| 5,912,175 A | | 6/1999 | Wille | |
| 6,001,654 A | | 12/1999 | Anderson et al. | |
| 6,093,531 A | | 7/2000 | Bjornson et al. | |

FOREIGN PATENT DOCUMENTS

| | | | |
|---|---|---|---|
| WO | 93/01275 | 1/1993 | ............ C12N/5/00 |
| WO | 94/09119 | 4/1994 | ............ C12N/5/08 |
| WO | 94/10292 | 5/1994 | ............ C12N/5/06 |
| WO | 94/16718 | 8/1994 | ............ A61K/37/00 |
| WO | WO 95/12665 | 5/1995 | |
| WO | 95/13364 | 5/1995 | ............ C12N/5/06 |
| WO | WO 97/41208 | 11/1997 | |
| WO | WO 99/56759 | 11/1999 | |

OTHER PUBLICATIONS

Sosnowski JS, Chemical traumatization of adult mouse olfactory epithelium in situ stimulates growth and differentiation of olfactory neurons in vitro. Brain Res. 1195 Dec. 8;702(1–2):37–48.*

Bamji, S. et al., "Comparison of the Expression of a Tα1:nlacZ Transgene and Tα1 α–Tubulin mRNA in the Mature Central Nervous System", J. Comp. Neurol. 374, 52(1996).

Bellows, CG et al., "Determination of Numbers of Osteoprogenitors present in Isolated Fetal Rat Calvaria Cells In Vitro", Dev. Biol. 133: 8–13 (1989).

Burns S et al., "A primate model of parkinsonism: Selective destruction of dopaminergic neurons in pars compacta of the substantia nigra by N–methyl–4–phenyl–1,2,3,6–tetra–hydropyridine", Proc Natl Acad Sci (USA) 80:4546–4550 (1983).

Calof et al., "Analysis of Neurogenesis in a Mammalian Neuroepithelium: Proliferation and Differentiation of an Olfactory Neuron Precursor in Vitro", Neuron 3:315 (1989).

Carlsson, A et al., "3,4–Dihydroxyphenylalanine and 5–Hydroxytryptophan as Reserpine Antagonists", Nature 180: 1200 (1957).

Dunnet, SB et al., "Nigral tranplants in primate models of parkinsonism", Intracereb. Transplant. Movem. Disord., ed. O. Lindvall et al., Restorative Neurology 4: 27–51(1991).

Ehringer, H. et al., "Verteilung von noradrenalin und dopamin (3–hydroxytyramin) im gehirn des menschen und ihr verhalten bei erkrankungen des extrapyramidalen systems", Kllin. Wschr. 38: 1236–1239 (1960).

Fahn S, "Fetal–tissue Transplants in Parkinson's Disease", New Eng. J. of Med. 327:1589–1590 (1992).

Friachard et al., "In vitro differentiation of embryonic stem cells glial cells and functional neurons", J. Cell. Sci. 108: 3181–3185 (1995).

Gage FH et al., "Survival and differentiation of adult neuronal progenitor cells transplanted to the adult brain", Proc Natl Acad Sci (USA) 92:118780–11883 (1995).

Gloster A et al., "THe Tα1 α–Tubulin Promoted Specifies Gene Expression as a Function of Neuronal Growth and Regeneration in Transgenic Mice", J. Neurosci. 14: 7319–7330 (1994).

Kaufman, S.J. et al., "Replicating myoblasts express a muscle–specific phototype", PNAS U 85: 9606–9610 (1988).

Langston JW, Ballard P, Tetrud JW, Irwin I, "Chronic Parkinsonism in Humans Due to a Product of Meperidine–Analog Synthesis", Science 219: 979–980 (1983).

LeGal La Salle, G. et al., "An Adenovirus Vector for Gene Transfer into Neurons and Glia in the Brain", Science 259: 988–990 (1993).

(List continued on next page.)

Primary Examiner—Yvonne Eyler
Assistant Examiner—Joseph F. Murphy
(74) Attorney, Agent, or Firm—Kristina Bieker-Brady; Clark & Elbing LLP

(57) ABSTRACT

This invention relates to multipotent neural stem cells, purified from the peripheral nervous system of mammals, capable of differentiating into neural and non-neural cell types. These stem cells provide an accessible source for autologous transplantation into CNS, PNS, and other damaged tissues.

8 Claims, No Drawings

OTHER PUBLICATIONS

Mayo, M.L. et al., "Desmin expression during early mouse tongue morphogenesis", Int. J. Dev. Biol. 36: 255–263 (1992).

Ourednik et al., "Neural stem cells– a versatile tool for cell replacement and gene therapy in the central nervous system", Clin. Genet. 56: 267–278 (1999).

Peel AL, Feldman DH, "Co–localization of glial and neuronal markers in RGF–generated cultures of pluripotent CNS stem cells", Society of Neuroscience Abstract 21: 285 (1995).

Reynolds et al., "Generation of Neurons and Astrocytes from Isolated Cells of the Adult Mammalian Central Nervous System", Science 255: 1707–1710 (1992).

Schubert, D. et al., "Ontogeny of electrically excitable cells in cultured excitable cells in cultured olfactory epithelium", PNAS U 82: 7782–7786 (1985).

Slack, R.S. and Miller, F.D., "Viral vectors for use in modulating gene expression in neurons", Curr. Opin. Neurobiot. 6:576–583 (1996).

Slack, Ruth S et al., "Adenovirus–mediated Gene Transfer of the Tumor Suppressor, p53, Induces Apoptosis in Postmitotic Neurons", J. of Cell Biol. 135 (4): 1085–1096 (1996).

Soriano, E. et al., "Simultaneous Immunocytochemical Visualization of Bromodeoyxuridine and Neural Tissue Antigens", J. Histochem. Cytochem. 39: 255–263 (1991).

Sosnowski, J.S. et al., "Chemical traumatization of adult mouse olfactory epithelium in situ stimulates growth and differentiation of olfactory nerves in vitro", Brain Res. 702: 37–48 (1995).

Ungerstedt, U. et al., "Quantitative Recording of Rotational Behavior in Rats after 6–Hydroxy–Dopamine Lesions of the Nigrostriatal Dopamine System", Brain Res. 24: 485–493 (1970).

Weiss, S. et al., "Is there a neural stem cell in the mammalian forebrain?", T.I.N.S. 19(9): 387–393 (1996).

Widner H et al., "Bilateral fetal mesencephalic grafting in two patients with parkinsonism induced by 1–methyl–4–phenyl–1,2,3,6–tetrahydropyridine (MPTP)", New England Journal of Medicine 3271556–1563 (1993).

Winkler C, Hammang JP, Bjorklund A, "EGF–responsive neural progenitor cells, survive, migrate and differentiate after transplantation into the adult rat striatum", Society for Neuroscience Abstracts 21: 2029 (1995).

Avoli, M. et al. Pharmacology and Electrophysiology of a Synchronous Gaba–Mediated Potential in the Human Neocortex. *Neurosci.* 62, 655–666 (1994).

Bruckenstein, D.A. & Higgins, D. Morphological Differentiation of Embryonic Rat Sympathetic Neurons in Tissue Culture. *Dev. Biol.* 128, 324–336 (1988).

Huard, J.M.T. et al. Adult Olfactory Epithelium Contains Multipotent Progenitors that Give Rise to Neurons and Non–Neural Cells. *J. Comp. Neurol.* 400, 469–486 (Nov. 2, 1998).

Taylor, G. et al. Involvement of Follicular Stem Cells in Forming Not Only the Follicle but Also the Epidermis. *Cell* 102, 451–461 (Aug. 18, 2000).

* cited by examiner

MULTIPOTENT NEURAL STEM CELLS FROM PERIPHERAL TISSUES AND USES THEREOF

CROSS REFERENCE TO RELATED APPLICATIONS

This application is a continuation-in-part of and claims priority from U.S. application Ser. No. 09/490,422, filed Jan. 24, 2000, which is a continuation-in-part of and claims priority from U.S. application Ser. No. 08/920,272, filed Aug. 22, 1997, which claims priority from U.S. Provisional Application Serial Nos. 60/024,590 and 60/024,456, filed Aug. 26, 1996, and Aug. 27, 1996, respectively, each of which is hereby incorporated by reference.

BACKGROUND OF THE INVENTION

The present invention relates to multipotent neural stem cells (MNSCs) purified from peripheral tissues containing sensory receptors such as the skin, olfactory epithelium, and tongue.

There are a number of diseases of the central nervous system ("CNS") which have a devastating effect on patients. These diseases are debilitating, often incurable, and include, for example, Alzheimer's disease, Huntington's disease, Parkinson's disease, and Multiple Sclerosis.

By way of example, Parkinson's disease is a progressive degenerative disorder of unknown cause. In healthy brain tissue, dopaminergic neurons extend from the substantia nigra of the brain into the neighboring striatum. In Parkinson's disease, these dopaminergic neurons die.

There are a number of methods to treat Parkinson's disease. One method is to treat humans having Parkinson's disease with L-DOPA. A second method is to transplant cells into the substantia nigra or striatum. Transplanted cells replace endogenous cells that are lost as a consequence of disease progression. An animal model of Parkinson's disease is an MPTP-treated non-human primate. The MPTP-treated animals have been transplanted with dopamine-rich embryonic neurons with some success.

To date, the cells used for neural transplant have been collected from the developing brains of aborted fetuses. Aside from the ethical considerations, the method from a practical standpoint is unlikely to provide a sufficient amount of neural tissue to meet the demands. Thus, another source of cells for transplantation is desirable.

Stem cells are undifferentiated cells that exist in many tissues of embryos and adult mammals. In embryos, blastocyst stem cells are the source of cells which differentiate to form the specialized tissues and organs of the developing fetus. In adults, specialized stem cells in individual tissues are the source of new cells, replacing cells lost through cell death due to natural attrition, disease, or injury. Stem cells may be used as substrates for producing healthy tissue where a disease, disorder, or abnormal physical state has destroyed or damaged normal tissue.

MNSCs may be used as a source of cells for transplantation. The MNSCs may themselves be transplanted or, alternatively, they may be induced to produce differentiated cells (e.g., neurons, oligodendrocytes, Schwann cells, or astrocytes) for transplantation. Transplanted stem cells may also be used as vectors for the expression of therapeutic molecules, such as growth factors, cytokines, anti-apoptotic proteins, and the like. Thus, stem cells are a potential source of cells for alternative treatments of diseases involving loss of cells or tissues.

The safest type of tissue graft (using stem cells or otherwise) is one that comes from self (an autologous tissue source). Autologous tissue sources are widely used in procedures such as bone transplants and skin transplants because a source of healthy tissue is readily accessible for transplant to a damaged tissue site. In brain diseases, such as Parkinson's disease, healthy dopaminergic neuronal brain tissue may exist at other sites in the brain, but attempts to transplant these neurons may harm the site where the healthy neurons originate. MNSCs that can be differentiated into dopaminergic neurons may be available at other sites from which they may be transplanted, but the CNS, particularly the brain, is physically difficult to access.

In several tissues, stem cells have been purified and characterized. For example, MNSCs have been purified from the mammalian forebrain (Reynolds and Weiss, Science 255:1707–1710, 1992) and these cells were shown to be capable of differentiating into neurons, astrocytes, and oligodendrocytes. PCT publications WO 93/01275, WO 94/16718, WO 94/10292 and WO 94/09119 describe uses for these cells. It could be impractical or impossible, however, to first access brain or other CNS tissue for biopsy and then again for transplant in patients with weakened health. It would be very useful if there were accessible stem cells capable of differentiating into CNS cell types, such as dopaminergic neurons; such cells would be a source of cells for autologous transplants.

Thus, there is a clear need to develop methods for identifying from accessible tissues neural stem cells that can act as a source of cells that are transplantable to the CNS, PNS, or other tissues in vivo in order to replace damaged or diseased tissue.

SUMMARY OF THE INVENTION

We have substantially purified MNSCs from the peripheral tissue of postnatal mammals, including juvenile and adult mammals. Most importantly, we have identified skin as a source of MNSCs and provide methods for the purification of skin-derived MNSCs, thus simplifying the harvesting of cells for transplantation relative to previous methods. The MNSCs possess desirable features in that they are multipotent and self-renewing. The cells can be repeatedly passaged and differentiated into cell types of the CNS, including astrocytes, oligodendrocytes, and neurons. The MNSCs express nestin, an immunological marker of neural stem cells and progenitor cells. The cells are capable of differentiating as dopaminergic neurons, and thus are useful source of dopaminergic neurons for homotypic grafts into Parkinson's Disease patients. The MNSCs may also make non-neural cells such as cardiac muscle cells, pancreatic islet cells, smooth muscle cells, hematopoietic cells, adipocytes, hepatocytes, and the like. The cells may also be used for autologous or heterologous transplants to treat, for example, other neurodegenerative diseases, disorders, or abnormal physical states.

Accordingly, in a first aspect, the invention features a MNSC substantially purified from a peripheral tissue of a postnatal mammal, wherein the peripheral tissue includes a sensory receptor.

In a second aspect, the invention features a cell that is the progeny of a MNSC substantially purified from a peripheral tissue of a postnatal mammal. The cell may be a mitotic cell or a differentiated cell (e.g., a neuron, an astrocyte, an oligodendrocyte, a Schwann cell, or a non-neural cell). Preferred neurons include neurons expressing one or more of the following neurotransmitters: dopamine, GABA, glycine, acetylcholine, glutamate, and serotonin. Preferred non-neural cells include cardiac muscle cells, pancreatic cells (e.g., islet cells), chondrocytes, osteocytes, skeletal muscle cells, smooth muscle cells, hepatocytes, hematopoietic cells, and adipocytes.

In a third aspect, the invention features a population of at least ten cells, wherein at least 30% of the cells are MNSCs substantially purified from a peripheral tissue of a postnatal mammal or progeny of the MNSCs, wherein the peripheral tissue includes a sensory receptor.

Preferably, at least 50% of the cells are MNSCs substantially purified from the peripheral tissue or progeny of the MNSCs. More preferably, at least 75% of the cells are MNSCs substantially purified from the peripheral tissue or progeny of the MNSCs. Most preferably, at least 90%, 95%, or even 100% of the cells are MNSCs substantially purified from the peripheral tissue or progeny of the MNSCs. The MNSCs may be cultured for extended periods of time. Thus, the population of cells may have been in culture for at least thirty days, sixty days, ninety days, or longer (e.g., one year or more). Preferably, the population is at least twenty cells, and may be more than fifty cells, a thousand cells, or even a million cells or more.

In a fourth aspect, the invention features a pharmaceutical composition including (i) a mitotic or differentiated cell that is the progeny of a MNSC substantially purified from a peripheral tissue of a postnatal mammal, wherein the peripheral tissue includes a sensory receptor, and (ii) a pharmaceutically acceptable carrier, auxiliary or excipient.

In a fifth, related aspect, the invention features a pharmaceutical composition including (i) a MNSC substantially purified from a peripheral tissue of a postnatal mammal, wherein the peripheral tissue includes a sensory receptor, and (ii) a pharmaceutically acceptable carrier, auxiliary or excipient.

Preferably, the composition of the fourth or fifth aspect includes a population of cells, wherein at least 30%, 50%, 75%, 90%, 95%, or even 100% of the cells are MNSCs substantially purified from the peripheral tissue or progeny of the MNSCs. The composition may include one or more types of cells selected from a group consisting of MNSCs, or neurons, oligodendrocytes, Schwann cells, and astrocytes which are progeny of MNSCs.

In a sixth aspect, the invention features a method of producing a population of at least ten cells, wherein at least 30% of the cells are MNSCs substantially purified from a peripheral tissue of a postnatal mammal or progeny of the MNSCs, wherein the peripheral tissue includes a sensory receptor, the method including: (a) providing the peripheral tissue from the mammal; (b) culturing the tissue under conditions in which MNSCs proliferate and in which at least 25% of the cells that are not MNSCs die; and (c) continuing culture step (b) until at least 30% of the cells are MNSCs or progeny of the MNSCs.

In a seventh aspect, the invention features another method of producing a population of at least ten cells, wherein at least 30% of the cells are MNSCs substantially purified from skin tissue of a postnatal mammal or progeny of the MNSCs, the method including: (a) providing the skin tissue from the mammal; (b) culturing the tissue under conditions in which MNSCs proliferate and in which at least 25% of the cells that are not MNSCs die; (c) separating the MNSCs from cells that are not MNSCs; and (d) repeating steps (b) and (c) until at least 30% of the cells are MNSCs or progeny of the MNSCs.

Suitable culture conditions for step (b) of the sixth and seventh aspects are preferably as follows: (i) triturating or otherwise mechanically separating tissue into single cells or cell clusters and placing into culture medium; (ii) culturing the cells in culture medium and under conditions (e.g., DMEM: Ham's F-12 medium containing B-27 supplement, antibacterial and antifungal agents, 5–100 ng/ml bFGF, and 2–100 ng/ml EGF) that allows for the proliferation of MNSCs but does not promote, to the same extent, proliferation of cells that are not MNSCs; and (iii) culturing the mechanically separated tissue for three to ten days, during which time the MNSCs proliferate in suspension but non-MNSCs do not proliferate in suspension (these cells either attach to the plastic or they die). Preferably, at least 50% of the cells in suspension surviving after the period in culture are MNSCs or progeny of the MNSCs, more preferably, at least 75% of the cells are MNSCs or progeny of the MNSCs, and, most preferably, at least 90% or even 95% of the surviving cells are MNSCs or progeny of the MNSCs.

In an eighth aspect, the invention features a method of treating a patient having a disease associated with cell loss. The method includes the step of transplanting the multipotent neural stem cells of the invention into the region of the patient in which there is cell loss. Preferably, prior to the transplanting step, the method includes the steps of providing a culture of peripheral tissue containing sensory receptors from the patient and isolating a multipotent neural stem cell from the peripheral tissue. After transplanation, the method may further include the step of differentiating (or allowing the differentiation of) the MNSCs into a desired cell type to replace the cells that were lost. Preferably, the region is a region of the CNS or PNS, but can also be cardiac tissue, pancreatic tissue, or any other tissue in which cell transplantation therapy is possible.

In a ninth aspect, the invention features a kit including a MNSC substantially purified from a peripheral tissue of a postnatal mammal, or a mitotic or differentiated cell that is the progeny of the MNSC, wherein the peripheral tissue from which the MNSC is purified includes a sensory receptor. Preferably, the kit includes a population of cells, wherein at least 30%, 50%, 75%, 90%, or even 95% of the cells are MNSCs substantially purified from the peripheral tissue or progeny of the MNSCs.

In a tenth aspect, the invention features a kit for purifying MNSCs from peripheral tissue containing sensory receptors. The kit includes media or media components that allow for the substantial purification of MNSCs of the present invention. The kit may also include media or media components that allow for the differentiation of the MNSCs into the desired cell type(s). Preferably, the kit also includes instructions for its use.

In one preferred embodiment of each of the foregoing aspects of the invention, the peripheral tissue is skin tissue. In another preferred embodiment, the peripheral tissue is olfactory epithelium or tongue tissue. In still another embodiment, the peripheral tissue of the first aspect specifically excludes olfactory epithelium and tongue tissue.

The peripheral tissue can be from a newborn mammal, a juvenile mammal, or an adult mammal. Preferred mammals include, for example, humans, non-human primates, mice, pigs, and rats. The MNSCs can be derived from peripheral tissue of any individual, including one suffering from a disease or from an individual immunologically compatible to an individual suffering from a disease. In a preferred embodiment, the cells, or progeny of the cells, are transplanted into the CNS or PNS of an individual having a neurodegenerative disease and the individual is the same individual from whom the MNSCs were purified. Following transplantation, the cells can differentiate into cells that are lacking or non-functional in the disease.

Preferably, the MNSCs express nestin and/or glutamic acid decarboxylase. The MNSCs of the present invention can, under appropriate conditions, differentiate into neurons, astrocytes, Schwann cells, oligodendrocytes, and/or non-neural cells (e.g., cardiac cells, pancreatic cells, smooth muscle cells, adipocytes, hepatocytes, etc.).

MNSCs can be stably or transiently transformed with a heterologous gene (e.g., one encoding a therapeutic protein, such as a protein which enhances cell divisions or prevents apoptosis of the transformed cell or other cells in the patient, or a cell fate-determining protein).

By "multipotent neural stem cell" or "MNSC" is meant a cell that (i) has the potential of differentiating into at least two cell types selected from a neuron, an astrocyte, and an oligodendrocyte, and (ii) exhibits self-renewal, meaning that at a cell division, at least one of the two daughter cells will also be a stem cell. The non-stem cell progeny of a single MNSC are capable of differentiating into neurons, astrocytes, Schwann cells, and oligodendrocytes. Hence, the neural stem cell is "multipotent" because its progeny have multiple differentiative pathways. The MNSC may also have the potential to differentiate as another cell type (e.g., a skin cell, a hematopoietic cell, a smooth muscle cell, a cardiac muscle cell, a skeletal muscle cell, or a pancreatic cell).

By "substantially purified" is meant that the desired cells (e.g., MNSCs) are enriched by at least 30%, more preferably by at least 50%, even more preferably by at least 75%, and most preferably by at least 90% or even 95%.

By "therapeutic protein" is meant a protein that improves or maintains the health of the cell expressing the protein or a that of a cell in proximity to the expressing cell. Example therapeutic proteins include, without limitation, growth factors (NGF, BDNF, NT-3, NT-4/5, HGF, TGF-β family members, PDGF, GDNF, FGF, EGF family members, IGF, insulin, BMPs, Wnts, hedgehogs, and heregulins) cytokines (LIF, CNTF, TNFM interleukins, and gamma-interferon), and anti-apoptotic proteins (LAP proteins, Bcl-2 proteins, Bcl-XL, Trk receptors, Akt, PI3 kinase, Gab, Mek, E1B55K, Raf, Ras, PKC, PLCγ, FRS2, rAPs/SH2B, and ΔNp73).

By "peripheral tissues containing sensory receptors" is meant a tissue that is not derived from neuroectoderm and specifically includes olfactory epithelium, tongue, skin (including dermis and epidermis), and mucosal layers of the body (e.g., mouth, reproductive system).

By a "population of cells" is meant a collection of at least ten cells. Preferably, the population consists of at least twenty cells, more preferably at least one hundred cells, and most preferably at least one thousand or even one million cells. Because of the MNSCs of the present invention exhibit a capacity for self-renewal, they can be expanded in culture to produce populations even billions of cells.

By "postnatal" is meant an animal that has been born at term.

By "a disease characterized by failure of a cell type" is meant one in which the disease phenotype is the result of loss of cells of that cell type or the loss of function of cells of that cell type.

Other features and advantages of the present invention will become apparent from the following detailed description and the claims. It will be understood, however, that the detailed description and the specific examples, while indicating preferred embodiments of the invention, are given by way of example only, and various changes and modifications within the spirit and scope of the invention will become apparent to those skilled in the art from this detailed description.

DETAILED DESCRIPTION OF THE INVENTION

We have substantially purified multipotent neural stem cells (MNSCs) from peripheral tissues of mammals, including skin, olfactory epithelium, and tongue. These cells proliferate in culture, so that large numbers of stem cells can be generated. These cells can be induced to differentiate, for example, into neurons, astrocytes, and/or oligodendrocytes by altering the culture conditions. They can also be induced to differentiate into non-neural cells such as smooth muscle cells, hematopoietic cells, adipocytes, hepatocytes, and the like. The substantially purified neural stem cells are thus useful for generating cells for use, for example, in autologous transplants for the treatment of degenerative disorders or trauma (e.g., spinal cord injury). In one example, MNSCs may be differentiated into dopaminergic neurons and implanted in the substantia nigra or striatum of a Parkinson's disease patient. In a second example, the cells may be used to generate oligodendrocytes for use in autologous transplants for the treatment of multiple sclerosis. In still another example, the MNSCs may be used to generate Schwann cells for treatment of spinal cord injury, cardiac cells for the treatment of heart disease, or pancreatic islet cells for the treatment of diabetes If desired, in any of the foregoing examples, the cells may be genetically modified to express, for example, a growth factor, an anti-apoptotic protein, or another therapeutic protein.

The MNSCs display some similarities to stem cells derived from mammalian forebrain, but also possess some distinctive differences. In particular, when the MNSCs of the present invention differentiate in the presence of serum, about 5–20% of the differentiated cells express neuronal markers, whereas differentiated forebrain stem cells generate only a small percentage of neurons. Moreover, significant numbers of dopaminergic neurons are found in differentiated cultures of MNSCs of the present invention, whereas such neurons have not been observed in cultures of forebrain stem cells differentiated in serum.

Cell Therapy

The MNSCs of this invention may be used to prepare pharmaceutical compositions that can be administered to humans or animals for cell therapy. The cells may be undifferentiated or differentiated prior to administration. Dosages to be administered depend on patient needs, on the desired effect, and on the chosen route of administration.

The invention also features the use of the cells of this invention to introduce therapeutic compounds into the diseased, damaged, or physically abnormal CNS, PNS, or other tissue. The MNSCs thus act as a vector to transport the compound. In order to allow for expression if the therapeutic compound, suitable regulatory elements may be derived from a variety of sources, and may be readily selected by one with ordinary skill in the art. Examples of regulatory elements include a transcriptional promoter and enhancer or RNA polymerase binding sequence, and a ribosomal binding sequence, including a translation initiation signal. Additionally, depending on the vector employed, other genetic elements, such as selectable markers, may be incorporated into the recombinant molecule. The recombinant molecule may be introduced into the stem cells or the cells differentiated from the stem cells using in vitro delivery vehicles such as retroviral vectors, adenoviral vectors, DNA virus vectors and liposomes. They may also be introduced into such cells in vivo using physical techniques such as microinjection and electroporation or chemical methods such as incorporation of DNA into liposomes. The genetically altered cells may be encapsulated in microspheres and implanted into or in proximity to the diseased or damaged tissue.

Preferably, the MNSCs are used for the treatment of neurological disease, but may be used as a source of non-neural cells. PCT publication WO99/16863 describes the differentiation of forebrain MNSCs into cells of the hematopoietic cell lineage in vivo. The MNSCs of the present invention appear to be more plastic and thus are highly likely to also be capable of differentiating into non-neural cells types, such as hematopoietic cells. Accordingly, the invention features methods of treating a patient having any disease or disorder characterized by cell loss by administering MNSCs of the present invention (or cells derived from these cells) to that patient and allowing the cells to differentiate to replace the cells lost in the disease or disorder. For example, transplantation of MNSCs and their progeny provide an alternative to bone marrow and hematopoietic stem cell transplantation to treat blood-related disorders. Other uses of the MNSCs are described in Ourednik et al. (Clin. Genet. 56:267–278, 1999), hereby incorporated by reference.

EXAMPLE 1

Purification of MNSCs from Postnatal Mouse Olfactory Epithelium

MNSCs from mouse olfactory epithelium were purified as described below. Postnatal mice were stunned with a blow to the head and then decapitated. The heads were sagitally sectioned with a razor blade, and the olfactory epithelia of about six postnatal (P1–P9) mouse pups were stripped from the conchae, nasal septum, and vomeronasal organs using watch-maker forceps. This tissue was placed into 3 mL of medium (DMEM/F-12 3:1) supplemented with 2% B-27 (Gibco, Burlington, Ontario, Canada), 20 ng/mL epidermal growth factor (EGF; Collaborative Research, Bedford, Mass.), 0.1% fungizone, and 0.5 mL/100 mL penicillin/streptomycin (Gibco). Following collection, the epithelia were teased apart with watchmaker forceps, releasing a large number of single cells and small cell clusters. The cell suspension was transferred to a 15 mL tube, and 7 mL of additional medium was added. The clusters were dissociated into single cells by titration with a 10 mL plastic pipette and passed through a 60 micron filter (Gibco). Typically, dissociated cells from the olfactory epithelia from six pups were plated into two 50 mL tissue culture flasks and cultured in a 37° C., 5% $CO_2$ tissue culture incubator. Two days later, most cells in the cultures were dead or dying. A small number (less than 1% of the initial cell number) of large, phase bright cells were present, however, most of which were attached to the flask bottom. Over the next two to six days, these cells divided and produced spherical clusters, which became larger over time. At four to five days in culture, there were approximately 500 clusters of dividing cells per pup used in the original purification. Most of these cell clusters detached from the flask surface over the next few days. These detached cell clusters continued to grow and fused together to become macroscopic, reaching approximately 100 µm in diameter following 10 DIV. After 12 DIV, the cell clusters became macroscopic, reaching approximately 200 µm or greater in diameter.

If EGF was not added to the medium, small clusters of dividing cells were still seen by 4 DIV, and some cell were formed, indicating that the cells themselves were producing trophic factors in quantities that, in some cases, was sufficient to maintain their proliferation.

Greater than 95% of the cells in the dividing clusters expressed nestin, a marker for neural progenitor cells and neural stem cells. These nestin-positive cells could be repeatedly passaged, indicating that the cells were neural stem cells. Six days after purification, the medium (5 mL) was removed from the flasks. This medium contained many clusters of stem cells that had detached from the flask surface. The detached cells were triturated with a fire-polished pipette, thereby dissociating many of the cell clusters into single cells. The medium containing the cells was then placed in a second flask with an additional 15 mL of fresh medium (total volume=20 mL). After a further six days, one quarter of the medium was removed and the detached clusters of cells were again triturated and transferred to a new flask with 15 mL fresh medium. These cells have been successfully passaged more than twenty times without losing their multipotency.

EXAMPLE 2

Differentiation of Mouse MNSCs Into Neurons, Astrocytes and Oligodendrocytes After the cellular clusters of Example 1 had been generated, they could be differentiated into neurons, astrocytes, and oligodendrocytes. Clusters from cultures 7 to 14 days after purification were plated onto polylysine coated 35 mm culture dishes or 4 multiwell culture dishes, in DMEM/F12 media containing 2% fetal bovine serum (Hyclone, Logan, Utah) and 2% B-27 (containing no EGF). The medium was changed every three to four days. Over the next six to nineteen days, cells migrated out of the clusters onto the dish surface. Some of these cells bad the morphology of neurons, astrocytes, or oligodendrocytes. We determined the phenotype of these cells using the following antibodies: GFAP for astrocytes; neurofilament 160 (NF-160), MAP-2, βIII tubulin, and NeuN for neurons; and GC for oligodendrocytes. Antibodies to TH were used to identify dopaminergic, noradrenergic, and adrenergic neurons. Dopamine β-hydroxylase (DBH) was also used for noradrenergic and adrenergic neurons.

Astrocytes, neurons, and oligodendrocytes were all found to differentiate from the neural stem cells, indicating that the cells were multipotent. We also cultured neural stem cells from transgenic mice which express β-galactosidase off of the neuron specific Tα1 α-tubulin promoter, which allowed us to use staining with the ligand X-gal antibodies for β-galactosidase as an additional neuronal marker. We observed β-galactosidase-positive cells.

Since the majority of differentiated cells remained in clusters, it was not possible to determine the percentage of cells expressing each marker. The majority of cells that migrated out of the clusters were GFAP positive, while a large number of cells were either NeuN or β-galactosidase positive. A lower number of cells were GC positive. Therefore the MNSCs could differentiate into neurons, astrocytes and oligodendrocytes. TH-positive cells were also identified. These TH-positive cells are most likely dopaminergic neurons and not noradrenergic or adrenergic neurons, since no cells were found to be DBH positive. Significantly, no TH, GFAP or GC positive cells have ever been reported in vivo in the nasal epithelium. Therefore the olfactory epithelium-derived nestin-positive MNSCs are capable of differentiating into cell types (e.g., oligodendrocytes, astrocytes, GABAergic neurons, and dopaminergic neurons) never found in the olfactory epithelium.

Like the originally-purified olfactory MNSCs, MNSCs passaged from two to twenty times could also differentiate into neurons, astrocytes, and oligodendrocytes. MNSCs which had been passaged were plated on polylysine-coated dishes. Cells migrated from the clusters and spread out over the surface of the dish. After 16 DIV, cells that were immunopositive for GC, GFAP, βIII tubulin, NeuN, lacZ, or TH could be identified. Moreover, the proportion of cells positive for the various markers was similar to that seen in the differentiated cultures from the original cultures.

EXAMPLE 3

Purification of MNSCs from Olfactory Epithelial Tissue of Adult Mice and Rats

Similar to the foregoing results, MNSCs were also purified from adult mouse and rat olfactory epithelium and vomeronasal organ using the methods described in Examples 1 and 2.

Adult mice and rats were anaesthetized with an overdose of somnitol, and then decapitated. The olfactory and vomeronasal organ epithelia were stripped from the conchae and nasal septum and incubated in DMEM/F12 medium for one to two days after their dissection and prior to the rest of the purification procedure. After this incubation, the epithelia were dissociated in an identical manner as the epithelia from juvenile mice. Two days after the isolation, the majority of the cells were dead with the exception of a very few large phase bright cells. These cells divided over the next few days, forming small clusters of dividing cells similar to those described in Example 1. These small clusters grew to give rise to the large clusters that detached from the culture dish surface. After approximately six divisions, cells in some of these clusters began to differentiate and spread out over the flask's surface, while some other clusters, which had been floating, reattached to the surface and then produced differentiated cells. In some cases, cells multiplied to produce small clusters of cells, but did not grow to form large cell clusters like the postnatal cultures. We have passaged these cells twenty times using the same procedure as that described above with respect to the cells purified from juvenile olfactory epithelium. These proliferating cells from the adult were also nestin-positive.

After the cell clusters derived from adult tissue had been generated, the cells could be differentiated into neurons, astrocytes, and oligodendrocytes. Seven days after isolation, clusters were plated onto polylysine-coated 35 mm culture dishes or multi-well culture dishes, in medium containing 2% fetal bovine serum and 2% B-27, but no EGF. Over the next month, cells migrated from the cell clusters and onto the dish surface. We determined the phenotype of these cells using antibodies to astrocytes, neurons, dopaminergic neurons, and oligodendrocytes as described above.

Neurons (including dopaminergic neurons), astrocytes, and oligodendrocytes were found, although the number of these cells was much lower than the number obtained from the juvenile. The cells purified from adult olfactory epithelia are self-renewing and multipotent, and thus are MNSCs.

EXAMPLE 4

Purification of MNSCs from Mouse Tongue

We derived MNSCs from the tongue, another peripheral tissue that contains sensory receptors. The tongue was dissected to remove the epithelial layer that contains the sensory receptors and their underlying basal cells. This layer of tissue was triturated to produce single cells and the single cells were plated in flasks containing DMEM/F12 media supplemented with B-27 and EGF, TGFα, and/or bFGF, as described for the olfactory epithelium. After two to three days in a 37° C., 5% $CO_2$ tissue culture incubator, greater than 99% of the cells in the culture were dead or dying. A small number (less than 1%) of large phase-bright cells were present, however, most of which attached to the flask bottom. Over the next two to six days, these cells divided and produced spherical clusters that became larger over time and detached from the flask surface. The cells in these clusters were nestin-positive.

These nestin-positive MNSCs can be passaged using the same techniques as used for the multipotent stem cells derived from the olfactory epithelium. Similarly, the MNSCs can be differentiated into neurons, astrocytes and oligodendrocytes using the techniques described herein.

EXAMPLE 5

Purification of MNSCs from Mouse Skin

Skin from neonatal mice aged 3–15 days was dissociated and cultured in uncoated flasks containing 20 mg/mL EGF and 40 mg/mL bFGF. Over the subsequent one to five days, many (>90%) of the cells die. A small population of cells hypertrophy and proliferate to form small cell clusters growing in suspension. Some of these cells first attach to the tissue cluster plastic, hypertrophy and proliferate, and then detach as the clusters become of sufficient size. Other cells never attach to the tissue culture plastic and instead proliferate in suspension from the beginning. After four to five days, the cell clusters are small but easily distinguishable as clusters of proliferating cells. By seven to ten days, many of the cell clusters reach diameters of as much as 100 $\mu$m, while by two weeks, the cell clusters are macroscopic if left unperturbed. Many cells adhered to the plastic, and many died, but by about three to seven days, suspended clusters of up to about 20 cells formed. These suspended or floating cells were transferred to a new flask seven days after initial culturing; again, many cells adhered, but the cells in the floating clusters proliferated to generate larger clusters of more than about 100 cells. These larger clusters were then isolated, dissociated and passaged. By this process of selective adhesion, pure populations of floating clusters were obtained after 3 to 4 weeks. Cells that generated these clusters were relatively abundant; 1.5 to 2 $cm^2$ of abdomen skin was sufficient to generate six 25 $cm^2$ flasks of floating clusters over this period of time.

To determine whether clusters contained MNSCs, we dissociated the clusters and plated the cells onto poly-D-lysine/laminin-coated dishes or chamber slides without growth factors and, 12 to 24 hours later, immunostained them for the presence of the neural precursor-specific marker nestin. After three passages, the majority of the cells expressed nestin, a property they maintained over subsequent passages. They did not, however, express the p75 neurotrophin receptor, a marker for neural crest stem cells, as detected either by immunocytochemistry or western blots.

To determine whether similar clusters could be generated from adults, skin of adult mice was dissociated and cultured as described above. Similar to neonatal mouse skin, most cells adhered to the flask or died when first cultured. After three to seven days, however, clusters of up to approximately 20 cells were observed that subsequently increased in size. When these cells were passaged at least three times, and plated onto poly-D-lysine/laminin overnight in the absence of growth factors, they too were immunopositive for nestin. The nestin-positive cells from adults and neonates have been passaged in this manner for over 30 passages, during which time the number would have theoretically expanded at least $10^9$-fold (assuming a doubling time of approximately one week).

To determine whether these nestin-positive cells from skin could generate neural cell types, we analyzed neonatal skin-derived cells after three or more passages and greater by plating them on poly-D-lysine/laminin in the absence of growth factors. Immunostaining and western blot analysis revealed that the skin-derived cells expressed neuronal markers. At seven days, a subpopulation of morphologically-complex cells coexpressed nestin and neuron-specific βIII-tubulin, a profile typical of newly-born neurons. At later timepoints of 7–21 days, cells also expressed neurofilament-M (NF-M) and neuron-specific enolase, two other neuron-specific proteins. Finally, some neurofilament-positive cells expressed GAD, a marker for GABAergic neurons, which are not found in the PNS. Similar results were obtained for adult skin-derived MNSCs, although at early passages some of the the βIII-tubulin and neurofilament-positive cells were less typically neuronal in morphology.

Immunostaining and western blots revealed that both neonatal and adult MNSCs generated cells expressing the glial markers GFAP and CNPase at seven to twenty-one days after plating. Double-labelling for these proteins demonstrated the presence of (i) cells that were GFAP-positive but not CNPase-positive (potentially astrocytes), (ii) cells that expressed CNPase but not GFAP (potentially oligodendrocytes or their precursors), and (iii) a small subpopulation that were bipolar and expressed both CNPase and GFAP (potentially Schwann cells). A subpopulation of GFAP-positive cells also expressed nestin, a finding previously reported for developing CNS astrocytes. Additionally, some cells were positive for A2B5, a marker for oligodendrocyte precursors. Like GAD-positive neurons, astrocytes and oligodendrocytes are normally found only in the CNS.

Double-labeling studies supported three additional conclusions. First, glial versus neuronal markers were expressed in distinct subpopulations of MNSCs progeny. Second, after twenty passages, skin-derive MNSCs were still able to differentiate into neurons and glial cells. Finally, skin-derived MNSCs were able to generate smooth muscle cells, as determined by both expression of smooth muscle actin (SMA) and morphology.

EXAMPLE 6

Purification of Nestin-positive Cells from Adult Human Skin

We have purified nestin-positive cells from human scalp. To purify MNSCs from human skin, we utilized tags of scalp tissue generated by placement of a stereotactic apparatus during neurosurgery. Scalp tags totalling 1 cm² or less from each of eight individuals were used. The skin included dermal and epidermal tissue. Tissue was cut into smaller pieces that were then transferred into HBSS containing 0.1% trypsin for forty minutes at 37° C. Following trypsinization, tissue samples were washed twice with HBSS and once with DMEM:F12 (3:1) supplemented with 10% rat serum to inactivate the trypsin. Trypsinized tissue was then mechanically dissociated by trituration in a pipette and the resulting dispersed cell suspension was poured through a 40 μm cell strainer into a 15 mL tube. The tube was then centrifuged for five minutes at 1000 rpm (~1200×g). The cells were resuspended in DMEM:F12 medium containing 40 ng/mL bFGF, 20 ng/mL EGF, 2% B-27 supplement, and antibacterial and antifungal agents, and then cultured in 12 well plastic tissue culture plates. Every seven days, the cell clusters are harvested by centrifugation, triturated with a fire-polished pasteur pipette, and cultured in fresh medium.

As for the use of rodent skin, most cells (>75%) adhered to the plastic or died, but after seven days, small floating clusters of cells were observed. These clusters were then partially dissociated and transferred to new wells, where they slowly increased in size. After additional passaging, clusters were plated on poly-D-lysine/laminin in 3% FBS with no growth factors, and analyzed for the presence of neural markers.

Within two weeks, greater than 30% of the cells within the cell clusters were nestin-positive. Immunolabeling of four to six week old cultures also revealed that many of the cells in the clusters were nestin-positive with the percentage varying from less than 50% to greater than 80% two to three days after plating. Double-label immunocytochemistry at the same or longer time-points revealed that, in all cultures, some nestin-positive cells also expressed βIII-tubulin and displayed elongated neurites. Thus, adult human skin is a source for nestin-positive MNSCs cells that, when differentiated, can express neuron-specific proteins.

EXAMPLE 7

Purification and Differentiation of MNSCs Derived from Other Human Peripheral Tissues Containing Sensory Receptors MNSCs can be purified from human olfactory epithelium using the same procedures as described for the purification of stem cells from rodent olfactory epithelium. Source material is acquired by surgical removal of olfactory epithelial tissue from the donor. Because the MNSCs are capable of proliferation and self-renewal, little source tissue is required. Preferably, the amount is at least about 1 mm³. Conditions for culturing human cells are described in Example 6, above. Other conditions are known to those skilled in the art, and can be optimized for proliferation or differentiation of neural stem cells, if desired.

We can purify MNSCs from other peripheral tissues containing sensory receptors, other than the olfactory epithelium, tongue, and skin, using techniques described herein. Passaging and differentiation of these cells is also performed using the same techniques described herein. Other peripheral tissues containing sensory receptors include, for example, mucosal membranes from the mouth or reproductive system.

EXAMPLE 8

Limiting Dilution Analysis of Purified MNSCs

To determine whether an individual cluster of cells is derived from a single MNSC, we performed a limiting dilution analysis using MNSCs derived from juvenile mouse olfactory epithelial tissue. This analysis demonstrates that the limiting dilution curve was linear, displaying single hit kinetics, indicating that individual cell clusters were most likely clones of single MNSCs. This analysis also demonstrates that cells capable of giving rise to clusters of MNSCs were present at a frequency of approximately one in 9000.

Thus, as >95%, of the cells in the clusters were nestin-positive, we conclude we enriched for peripheral tissue-derived stem calls by at least 450-fold. Differentiation of these individual clusters demonstrated that individual cells were multipotent. Specifically, double-label immunocytochemistry revealed that cell clusters derived from single MNSCs were capable of generating astrocytes, oligodendocytes, and TH-positive neurons.

EXAMPLE 9

Transformation of MNSCs

In therapy for neurodegenerative diseases, it may be desirable to transplant cells that are genetically modified to survive the insults that caused the original neurons to die. In addition, MNSCs may be used to deliver therapeutic proteins into the brain of patients with neurodegenerative disorders to prevent death of host cells. Examplary therapeutic proteins are described herein. In still another example, MNSCs can be induced to differentiate into a desired cell type by transforming the cells with nucleic acid molecules encoding proteins that regulate cell fate decisions (e.g., transcription factors such as Isl-1, en-1, en-2 and nurr-1, implicated in regulating motomeuron and striatal phenotypes). Using such a method, it is possible to induce the differentiation of the specific cell types required for transplant therapy. Therefore, it would be advantageous to transform MNSCs with nucleic acid molecules encoding desired proteins. We have previously used recombinant adenovirus to manipulate both postmitotic sympathetic neurons and cortical progenitor cells, with no cytotoxic effects. We now have established that olfactory epithelial-derived MNSCs and skin-derived MNSCs can each be successfully transfected with high efficiency and low toxicity.

EXAMPLE 10

Differentiation of MNSCs Into the Appropriate Cell Type in vivo Following Transplantion Into Adult Rodent Brain One therapeutic use for the MNSCs of the present invention is autologous transplantation into the injured or degenerating CNS or PNS to replace lost cell types and/or to express therapeutic molecules. We demonstrate below that the MNSCs can differentiate into neurons when transplanted into the adult brain.

If desired, the dopaminergic innervation of the adult striatum can be unilaterally destroyed by a local infusion of 6-hydroxydopamine under conditions in which noradrenergic neurons are spared. Several weeks later, MNSCs are transplanted into both the intact and lesioned striatum. Altenatively, the cells can be transplanted into unlesioned animals. The fate of the transplanted MNSCs is then determined by immunohistochemistry. Exemplary transplantation studies are described below. These studies demonstrate that transplanted MNSCs can differentiate into neurons in vivo, as they can in vitro. In the former case, differentiation and cell fate choice is controlled by the local environment into which each cell is placed. Both in vitro-differentiated and undifferentiated cells are useful therapeutically in the treatment, for example, of neurodegenerative disease (e.g., Parkinson's disease and multiple sclerosis) or spinal cord injury. For example, dopaminergic neurons differentiated from MNSCs, or the MNSCs themselves, may be transplanted into the substantia nigra or the striatum of patients having Parkinson's disease. If desired, the MNSCs may also be genetically-modified to express a desired protein.

In one example, the dopaminergic innervation to adult rat striatum was first unilaterally lesioned with the chemotoxin 6-hydroxydopamine, and the efficacy of the lesions was tested two weeks later by amphetamine-induced rotational behavior. Two days prior to transplantation, rats were immunosuppressed with cyclosporin. MNSCs, produced from olfactory epithelia as described herein, were then stereotactically injected into the caudate-putamen complex on both the lesioned and unlesioned sides. Sixteen days following transplantation, animals were sacrificed, and sections of the striatum were analyzed for nestin- and TH-immunoreactivity. Five of eight animals received successful injections of MNSCs in the striatum. Of these, four animals showed evidence of a nestin-positive tract on both the lesioned and unlesioned sides, although tracts on the lesioned side appeared to be more intensely nestin-immunoreactive. On adjacent sections, TH-positive cells were observed confined to an area close to the transplant tract on both the lesioned and unlesioned side. As many as 25–30 TH-positive cells were identified on each section. Cell morphology varied from small, round cells lacking processes to neurons that were morphologically complex with multiple fine processes. In some cases, the processes of these TH-positive neurons extended into the striatum for distances of up to 300 µm.

To confirm that these TH-positive neurons derived from the MNSCs, we performed two sets of experiments in which the transplanted cells were detectably-labeled. In one set of experiments, transplanted MNSCs were derived from Tα1:nlacZ transgenic mice, in which the neuron-specific Tα1 α-tubulin promoter drives expression of a nuclear-localized β-galactosidase marker gene. Immunohistochemical analysis of animals receiving the transgenic MNSCs revealed the presence of β-galactosidase-positive neurons within the transplant tract, confirming that the transplanted MNSCs generated neurons in vivo, as they did in vitro. In a second set of experiments, MNSCs were labelled with BrdU for 18 hours, washed to remove the BrdU label, and then transplanted unilaterally into the 6-hydroxydopamine-lesioned striatum of animals (10 rats, 4 mice) prepared as described herein. Immunohistochemical analysis with anti-BrdU revealed that all animals showed evidence of BrdU-positive transplant tracts. Immunocytochemistry with anti-GFAP revealed that, in both xenografts and allografts, GFAP-positive cells with heterogeneous morphology were concentrated at the transplant site, but were also present in moderate amounts over the entire ipsilateral hemisphere, with additional scattered reactive astrocytes seen in the contralateral hemisphere. GFAP-BrdU double-labelled cells were present mainly within or close to the transplant tract, and varied in morphology from small, round cells with only a few processes, to large polygonal or fusiform cells with multiple processes. Immunohistochemistry with anti-TH revealed that TH-BrdU double-labeled cells were also present, although these were few in number relative to GFAP-BrdU positive cells. BrdU-TH double-labeled cells were mainly small to medium-sized without processes, although some examples of double-labeled cells with processes were found within and adjacent to, the transplant tract. Thus, MNSCs generated astrocytes and neurons in vivo, and a subpopulation of the latter were TH-positive. Together, these findings show that peripheral tissue-derived MNSCs are capable of generating cell types that are never found within olfactory tissue, including oligodendrocytes and TH-positive neurons.

To determine whether skin-derived MNSCs also generate differentiated neural cell types in vivo, we tagged adult mouse skin-derived MNSCs with (i) BrdU, and (ii) a recombinant adenovirus expressing GFP, and then transplanted them as cell clusters of about 20 to about 100 cells into the lateral ventricles of P2 rats. Immunostaining fourteen days later revealed that, in all animals analyzed (n=8), transplanted cells had migrated extensively. In particular, tagged cells had integrated into the cortex, the hypothalamus and the amygdala in all, and into the hippocampus in two of the transplanted brains. In the cortex, GFP-positive cells were located in patches, or occasionally as single cells, including some that had integrated into and adopted the morphology of layer V pyramidal neurons. These cells had triangular-shaped soma, and projected a presumptive apical dendrite from layer V towards layer I, in a manner similar to the endogenous layer V neurons. That these cells were neurons was demonstrated by double-labeling for neuron-specific enolase. Immunocytochemical analysis also confirmed that these were transplanted cells, as BrdU-positive cells were present in the same locations as GFP-positive cells in all brains.

In both the amygdala and hippocampus, transplanted cells also displayed neuronal morphology. In the amygdala, GFP and BrdU-positive cells were large, with prominent nuclei, and extensive processes. In the hippocampus, transplanted cells had integrated into both the dentate gyrus and pyramidal cell layers, and their morphology was typical of the endogenous granule and pyramidal cells, respectively. GFP-positive staining was also seen within the molecular layer. Finally, GFP- and BrdU-positive cells were observed in other locations, such as the hypothalamus, where the morphology of many cells was not typically neuronal.

Skin-derived MNSCs tranplanted into adult rats also survive and fintegrate. We labeled adult mouse skin-derived MNSCs that had been passaged more than thirty times with the nuclear dye 33258, washed extensively, and then injected the cells stereotactically into the brains of adult rats that were immunosuppressed with cyclosporin. Four weeks later, we sacrificed the animals by perfusion and processed the brains for histological examination. Hoeschst-labeled cells were present in the hippocampus, olfactory bulb, and striatum. From these data, we conclude that the transplanted skin-derived MNSCs are capable of survival following transplantation. Moreover, cells are capable of migrating from the site of injection to numerous brain regions.

Skin-derived MNSCs are also capable of survival, migration, and integration following transplantation into a hemisected adult mouse spinal cord. In this example, the cells were injected into the injured sides of hemisected spinal cords. Eight days later, the animals were sacrificed and the spinal cords processed for histological analysis. Hoechst-labeled cells were present at the site of the initial injection, and had also migrated extensively into the injured spinal cord.

EXAMPLE 11

Differentiation of Non-neural Cells from MNSCs

In addition to being capable of differentiating as neural cells (i.e., neurons, oligodendrocytes, astrocytes, and Schwann cells), the peripheral tissue-derived MNSCs are capable of differentiating as non-neural cells that are normally not found in the tissue from which the cells were derived. For example, we have demonstrated that the skin-derived MNSCs can differentiate as smooth muscle cells and adipocytes. It is likely that the cells described herein have even greater potential. Conditions for the differentiation of the MNSCs into smooth muscle cells is described herein.

Signals or conditions sufficient for inducing MNSCs to differentiate as other cell types (e.g., lymphocytes, cardiac muscle cells, skeletal muscle cells, melanocytes, and pancreatic cells) are known in the art. For example, unique signals induce neural crest-derived MNSCs to become melanocytes, cartilage, smooth muscle cells, or bone (for review, see LaBonne and Bronner-Fraser, J. Neurobiol., 36:175–189, 1998; Sieber-Blum, Intl. Rev. Cytol. 197:1–33, 2000). Conditions for inducing CNS-derived MNSCs to differentiate as non-neural cells such as smooth muscle cells, skeletal muscle cells, hepatocytes, hematopoietic cells, osteocytes, and chondrocytes have similarly been elucidated (Bjornson et al., Science 283:534–537, 1999; Tsai and McKay, J. Neurosci. 20:3725–3735, 2000; Keirstead et al., J. Neurosci. 19:7529–7536, 1999; Mujtaba et al., Dev. Biol. 200:1–15, 1998; Clark et al., Science 288:1660–1663, 2000).

The recent discovery that MNSCs maintained the potential to produce both neural and non-neural cell types has been accompanied by the discovery that non-neural stem cells such as bone marrow-derived stem cells (i.e., stromal cells or mesenchymal stem cells) also have the potential to produce a wide variety of neural and non-neural stem cells (Ferrari et al., Science 279:1528–1530, 1998; Gussoni et al., Nature 401:390–394, 1999; Peterson et al., Science 284:1168–1170, 1999; Pereira et al., Proc. Natl. Acad. Sci. USA 92:4857–4861, 1995; Prockop, Science 276:71–74, 1997; Kessler and Byrne, Annu. Rev. Physiol. 61:219–242, 1999; Pittenger et al., Science 284:143–147). The conditions under which these bone marrow-derived cells differentiate as, for example, skeletal muscle cells, cardiac muscle cells, hepatocytes, adipocytes, osteocytes, or chrondrocytes are likely to be conditions under which the peripheral tissue-derived MNSCs would differentiate similarly. Thus, the peripheral tissue-derived MNSCs described herein can be induced to differentiate into both neural and non-neural cells that are not normally found in the tissue from which the MNSCs were derived.

The foregoing experiments were performed using the following methods.

Skin-derived MNSC Culture

For neonatal (three to 14 days) and adult (two months to one year) mice, skin from abdomen and back was carefully dissected free of other tissue, cut into 2–3 $mm^3$ pieces, washed three times in HBSS, and then digested with 0.1% trypsin for 40 minutes at 37° C., followed by 0.1% DNAase for one minute at room temperature. Tissue pieces were then washed twice with HBSS, once with media (DMEM-F12, 3:1, 1 $\mu$g/ml fungizone, 1% penicillin/streptomycin) containing 10% rat serum (Harlan Bioproducts), and twice with serum-free media. Skin pieces were then mechanically dissociated in media, and the suspension poured through a 40 $\mu$M cell strainer (Falcon). Dissociated cells were centrifuged, and resuspended in 10 ml media containing B-27 supplement, 20 ng/ml EGF and 40 ng/ml bFGF (both Collaborative Research). Cells were cultured in 25 $cm^2$ tissue culture flasks (Corning) in a 37° C., 5% $CO_2$ tissue culture incubator.

To culture human skin-derived MNSCs, two to three pieces of scalp tissue ranging between 4–9 $mm^2$ (generated by placement of the stereotaxic apparatus for neurosurgery) were washed with HBSS, any subcutaneous tissue was removed, and the skin was cut into small pieces 1–2 $mm^3$ in size. Tissue pieces were transferred to 15 mL Falcon tubes, washed three times with HBSS, and enzymatically digested in 0.1% trypsin for 40 minutes at 37° C., and then washed as for mouse tissue. Dissociated cells were suspended in 5 mL of the same media used for mouse cultures, with the addition of 20 ng/ml LIF (R&D Systems Inc.). The cell suspension was placed in Falcon 6-well tissue culture plates and maintained in a 37° C., 5% $CO_2$ tissue culture incubator. Cells were subcultured by partial dissociation of the clusters that formed every 7 to 10 days.

To passage floating clusters of cells, the medium containing the cell clusters was centrifuged, the cell pellet mechanically dissociated with a fire-polished Pasteur pipette, and the cells reseeded in fresh media containing B-27 supplement and growth factors as above. Cells were passaged every 6 to 7 days. For induction of differentiation into neural cells, the cell clusters were centrifuged, the growth factor-containing supernatant removed, and the clusters resuspended in fresh media containing B-27 supplement and either 3% rat serum or 1–3% fetal bovine serum. The clusters were then plated onto 4-well Nunclon culture dishes coated with poly-D-lysine/laminin, and the medium was changed every 3 to 7 days.

Transplantation of Olfactory Epithelium-derived MNSCs

Olfactory epithelium-derived MNSCs were purified and cultured as described herein. Female Sprague-Dawley rats or CD1 albino mice (Charles River, Montreal, Quebec, Canada) weighing 180–200 g or 25–30 g, respectively, were anaesthetized with a mixture of ketamine (90 mg/kg) and xylazine (10 mg/kg) (intraperitoneal) prior to stereotactic injections of 24 $\mu$g of 6-hydroxydopamine hydrobromide (dissolved in 5 $\mu$L of 0.9% saline containing 0.2 mg/ml ascorbate) into the right medial forebrain bundle (Tooth bar: −2.4 mm; A: −4.4 mm; L: 1.0 mm; V: 7.5 mm). Two weeks after the lesion, animals were tested for rotational behavior. Animals were immunosuppressed with cyclosporine (40 mg/kg, intraperitoneal) once a day until the day of sacrifice. For MNSC transplantation, anaesthetized animals were mounted in a Kopf stereotactic apparatus, and 2×2.5 $\mu$L aliquots of MNSCs were injected unilaterally into the lesioned caudate putamen or bilaterally in some animals. The injections were made using a 5 $\mu$L Hamilton syringe at the following coordinates: Tooth bar, −2.4 mm; A: 0.2; L: 3.0; V: 5.5–6.0. Injections were performed over a period of three minutes, a further five minutes was allowed for diffusion, and the needle was then retracted. These 5 $\mu$L injections contained MNSCs derived from one neonatal pup cultured for 7 to 14 days. For the BrdU experiments, BrdU (10 $\mu$M) was added to culture media for 18 hours, after which the MNSCs were washed three times with fresh media to remove the BrdU, and then transplanted one day later.

Transplantation of Skin-derived MNSCs

Labeling of skin-derived MNSCs was performed as follows. Three days prior to transplantation, free-floating cell clusters were partially dissociated by gentle trituration, and then exposed to 50 MOI of a recombinant adenovirus expressing GFP, using standard techniques. Twenty-four hours later, the MNSCs were centrifuged, washed, and resuspended in fresh medium containing 2 $\mu$M BrdU for an additional two days. Prior to transplantation, MNSCs were rinsed five times with fresh medium and resuspended to a concentration of 50,000 cells/$\mu$l. At the time of transplantation, approximately 75% of the MNSCs expressed GFP, while 95% were BrdU positive.

MNSCs labeled with BrdU and GFP were stereotaxically injected into the right lateral ventricle of cryoanaesthetized two day old rat pups (co-ordinates from Bregma: lateral 1.5 mm, ventral 3.3 mm). Approximately 50,000 cells were injected over a three minute period in a volume of 1 $\mu$L. Fourteen days following transplantation, mice were perfused with 50 mL 4% formaldehyde buffered with PBS. Fifty micron coronal sections through the forebrain were cut using a freezing microtome and analyzed immunocytochemically. All eight animals receiving cell transplants showed extensive labeling for tagged cells. No evidence of tumor formation was observed.

Immunostaining

Immunostaining of olfactory epithelium-derived MNSCs was performed as follows. With the exception of GC immunocytochemistry, culture dishes were washed twice with Tris-buffered saline (TBS; 10 mM Tris, 150 mM NaCl, pH 8), then fixed with 4% formaldehyde, washed three times with TBS, blocked with TBS plus 2% goat serum (Jackson ImmunoResearch, Mississuagua, Ontario, Canada), and 0.1% Triton-X (Sigma Chemicals, St. Louis Mo.) for 30 minutes, then incubated with primary antibody in TBS plus 2% goat serum. Following primary antibody incubation, the dishes were washed three times with TBS, incubated in secondary antibody in TBS plus 2% goat serum, washed three times, and then viewed with a fluorescence inverted microscope. The antibodies to GFAP (Boehringer Mannheim, Laval, Quebec, Canada), $\beta$III tubulin (Sigma), NeuN (Dr. R. Mullen), MAP-2 (clone AP-20; Sigma), and NF-160 (American Tissue Culture Collection, Manassas Va.) were monoclonal antibodies used at concentrations of 1:200; 1:25; 1:10, and 1:1 respectively. Antibodies to nestin (a gift from Dr. Ron MacKay (National Institutes of Health), TH (Eugenetech Eugene, Oreg.), and DBH (Eugenetech) were rabbit polyclonal antibodies used at concentrations of 1:1000, 1:200, and 1:200 respectively. Secondary antibodies Cy3 conjugated goat anti-mouse (Jackson ImmunoResearch) and Cy3 conjugated goat anti-rabbit (Jackson ImmunoResearch), and were used at 1:1500. For double-labelling experiments, we used FITC goat anti-mouse (Jackson ImmunoResearch).

For GC immunocytochemistry, living cultures were incubated in DMEM containing HEPES, 5% heat inactivated horse serum (HS), and 1:10 GC antibody for 30 min at 37° C., washed three times with the medium/HEPES/HS, fixed with 4% formaldehyde for 15 minutes, rinsed three times in TBS, incubated in Cy3 conjugated goat anti-mouse antibody (1:1500) for two hours, and finally washed three times in TBS. Cultures processed for immunocytochemistry without primary antibodies revealed no staining.

Immunocytochemical analysis of cultured skin-derived MNSCs was performed as follows. The primary antibodies that were used were: anti-nestin polyclonal (1:250, Dr. Ron McKay, NINDS), anti-nestin monoclonal (1:400, PharMingen Inc.), anti-$\beta$III-tubulin monoclonal (1:500, Tuj1 clone, BabCo), anti-neurofilament-M polyclonal (1:200, Chemicon Intl.), anti-GAD polyclonal (1:800, Chemicon Intl.), anti-NSE polyclonal (1:2000, Polysciences Inc.), anti-GFAP polyclonal (1:200, DAKO), anti-CNPase monoclonal (1:400, Promega Inc.), anti-p75NTR polyclonal (1:500, Promega Inc.), anti-SMA monoclonal (1:400, Sigma-Aldrich Inc.), and anti-A2B5 monoclonal (Dr. Jack Snipes, M.N.I.). The secondary antibodies were Cy3-conjugated goat anti-mouse (1:200), Cy3-conjugated goat anti-rabbit (1:400), FITC-conjugated goat anti-mouse (1:50–1:100), and FITC-conjugated goat anti-rabbit (1:200) (all from Jackson Immunoresearch Laboratories Inc.).

Immunocytochemical analysis of free-floating brain sections was performed by DAB immunohistochemistry. For GFP, sections were incubated in 0.3% $H_2O_2$ for one hour to inhibit endogenous tissue peroxidase activity prior to blocking. For BrdU immunohistochemistry, sections were pre-incubated in 0.5% sodium borohydride for 20 minutes prior to blocking of endogenous peroxidase activity in 0.03% $H_2O_2$ for 30 minutes. To permeabilize the nuclei for BrdU immunohistochemistry, sections were incubated in 1% DMSO for 10 minutes, the DNA denatured with 2N HCl for 60 minutes, and the HCl neutralized with 0.1 M borate buffer for 5 minutes. All sections were blocked for one hour in 10% BSA, and then incubated for 48 hours at 4° C. with either anti-GFP (1:1000, Clontech) or anti-BrdU (1:100, Becton-Dickinson). Primary antibodies were detected using a biotinylated horse anti-mouse secondary antibody (1:200, Vector Laboratories) for one hour at room temperature, and visualized using the Vectastain kit (Vector Laboratories) and a nickel-enhanced DAB reaction containing 0.05% DAB, 0.04% nickel chloride, and 0.015% $H_2O_2$. Sections were mounted onto slides, dehydrated through a series of ethanols and Histoclear (Fisher Scientific), and coverslipped using Permount (Fisher Scientific).

Fluorescence immunohistochemistry was performed to co-localize GFP expression with NSE. Free-floating sections were blocked in 10% BSA for one hour at room temperature, and then incubated 48 hours at 4° C. in a solution containing mouse anti-GFP and rabbit anti-NSE. Sections were incubated with Cy3 conjugated anti-mouse and FITC conjugated anti-rabbit secondary antibodies for one hour at room temperature, and coverslipped using Sigma Mounting Medium.

Other Embodiments

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A method of producing a population of at least ten cells, wherein at least 30% of the cells are multipotent stem cells substantially purified from skin or tongue tissue of a postnatal mammal or progeny of said multipotent stem cells, wherein said multipotent stem cells are self-renewing, form non-adherent clusters, express nestin, and can differentiate into neuronal and mesodermal cell types, said method comprising the steps of:

(a) providing skin or tongue tissue from said mammal;

(b) culturing said skin or tongue tissue under conditions comprising bFGF, EGF or TGFα in which multipotent stem cells proliferate and in which at least 25% of the cells that are not multipotent stem cells die or attach to the culture substrate; and (c) continuing culture step (b) until at least 30% of the cells are multipotent stem cells which are self renewing, form non-adherent clusters, express nestin and can differentiate into neuronal and mesodermal cell types, or progeny of said multipotent stem cells.

2. A method of producing a population of at least ten cells, wherein at least 30% of the cells are multipotent stem cells substantially purified from skin or tongue tissue of a postnatal mammal or progeny of said multipotent stem cells, wherein said multipotent stem cells are self-renewing, form non-adherent clusters, express nestin, and can differentiate into neuronal and mesodermal cell types, said method comprising the steps of:

(a) providing skin or tongue tissue from said mammal;

(b) culturing said skin or tongue tissue under conditions comprising bFGF, EGF or TGFα in which multipotent stem cells proliferate and in which at least 25% of the cells that are not multipotent stem cells die or attach to the culture substrate;

(c) separating said multipotent stem cells from said cells that attach to said culture substrate; and (d) repeating steps (b) and (c) until at least 30% of the cells are multipotent stem cells which are self renewing, form non-adherent clusters, express nestin, and can differentiate into neuronal and mesodermal cell types, or progeny of said multipotent stem cells.

3. The method of claim 1, wherein said tissue is skin tissue.

4. The method of claim 1, wherein said mammal is a human.

5. The method of claim 4, wherein said tissue is skin tissue.

6. The method of claim 2, wherein said tissue is skin tissue.

7. The method of claim 2, wherein said mammal is a human.

8. The method of claim 7, wherein said tissue is skin tissue.

* * * * *